(12) United States Patent
Nagao et al.

(10) Patent No.: US 9,759,647 B2
(45) Date of Patent: Sep. 12, 2017

(54) WEAR-PROOF TESTER FOR RETAINER IN NEEDLE CAGE

(71) Applicant: NIPPON THOMPSON CO., LTD., Tokyo (JP)

(72) Inventors: Shoji Nagao, Kamakura (JP); Akihide Yanagitani, Kamakura (JP)

(73) Assignee: NIPPON THOMPSON CO., LTD., Tokyo (JP)

( * ) Notice: Subject to any disclaimer, the term of this patent is extended or adjusted under 35 U.S.C. 154(b) by 143 days.

(21) Appl. No.: 14/852,786

(22) Filed: Sep. 14, 2015

(65) Prior Publication Data
US 2016/0178505 A1 Jun. 23, 2016

(30) Foreign Application Priority Data

Dec. 18, 2014 (JP) ................................. 2014-256179

(51) Int. Cl.
*G01N 3/56* (2006.01)
*F16C 19/44* (2006.01)
*G01N 19/02* (2006.01)

(52) U.S. Cl.
CPC .............. *G01N 19/02* (2013.01); *G01N 3/56* (2013.01)

(58) Field of Classification Search
CPC ...... F16C 19/44; F16C 19/463; F16C 19/466; G01N 3/56; G01N 2203/0246; G01N 2203/0037; G01N 13/021
See application file for complete search history.

(56) References Cited

U.S. PATENT DOCUMENTS

| | | | | |
|---|---|---|---|---|
| 3,324,708 A | * | 6/1967 | Staph | F16C 19/00 374/153 |
| 5,520,467 A | * | 5/1996 | Nojima | F16C 19/26 384/463 |
| 5,725,688 A | * | 3/1998 | Sugi | C22C 38/001 148/318 |
| 6,094,967 A | * | 8/2000 | Cavdar | G01N 19/02 73/9 |

(Continued)

FOREIGN PATENT DOCUMENTS

| | | | | |
|---|---|---|---|---|
| DE | 102007031867 A1 | * | 1/2009 | ............. G01N 19/02 |
| JP | 0424531 A | | 1/1992 | |

(Continued)

*Primary Examiner* — David A Rogers
(74) *Attorney, Agent, or Firm* — Browdy and Neimark, PLLC

(57) ABSTRACT

A wear-proof tester to evaluate an anti-frictional performance of surface treatment carried on a needle cage. The needle cage is subjected to flex under the centrifugal force of composite revolution and rotation. Wear-proof test of surface treatment is carried by sliding contact between the outside circular surface of the retainer and the inside circular surface of the outside wheel. The retainer with no roller is fastened on a rotary shaft with leaving a clearance between them. A radial load is applied to retainer through a test outside wheel to get the retainer flexed to make sliding contact over a predetermined area between the outside circular surface of the retainer and the inside circular surface of the outside wheel. This wear-proof tester is applicable to the wear-proof tests of various materials other than the wear-proof test of the retainer made of various materials.

11 Claims, 9 Drawing Sheets

(56) References Cited

U.S. PATENT DOCUMENTS

| | | | | |
|---|---|---|---|---|
| 6,431,761 B1* | 8/2002 | Yamaguchi | ............... | C23C 8/26 |
| | | | | 384/527 |
| 8,449,200 B2* | 5/2013 | Egami | .................... | B82Y 30/00 |
| | | | | 384/294 |
| 9,086,094 B2* | 7/2015 | Egami | ........................ | F16C 9/02 |
| 9,163,659 B2* | 10/2015 | Sato | .......................... | F16C 9/02 |
| 9,581,537 B2* | 2/2017 | Beau | .................... | G01M 13/005 |

FOREIGN PATENT DOCUMENTS

| | | |
|---|---|---|
| JP | 1164167 A | 3/1999 |
| JP | 2005091212 A | 4/2005 |
| JP | 2014202639 A | 10/2014 |

* cited by examiner

WEAR-PROOF TESTER FOR RETAINER IN NEEDLE CAGE

FIELD OF THE INVENTION

The present invention relates to a wear-proof tester to evaluate an anti-frictional performance of surface treatment carried on a needle cage which is, for example, incorporated in a big end of a connecting rod used in a four-stroke-cycle engine.

BACKGROUND OF THE INVENTION

The needle cage used in engines generally is incorporated in a big end of a connecting rod and mainly composed of more than one needle roller and a retainer to keep in place the needle rollers. With the needle cage incorporated in the connecting rod, the retainer keeping the rollers therein would be subjected to flexing force under a large centrifugal force exerted during revolution of a crank shaft.

The retainer while subjected to centrifugal force makes revolution to make sliding contact with an inside circumference of the big end of the connecting rod. To cope with this, the outside circular surface of the retainer generally is applied with any plated layer such as cupper-plated layer, silver-plated layer and so on.

A tester to apply a centrifugal force to a bearing specimen has been developed and disclosed in, for example, Published Unexamined senior Patent Application in Japan No. H04-24 531. The prior tester is one of centrifugal load bearing testers and envisaged to carry out duration test of the retainer under lubrication conditions of mainly two-stroke-cycle engine. Especially, this tester is developed for a needle cage which is incorporated between the big end of the connecting rod and the crank pin in the engine. The tester is envisaged for the bearing which is subjected to a large centrifugal force caused by both spinning on its axis and revolution. This tester is designed to make sliding contact with the outside circumference of the retainer of the needle cage to carry out evaluation of an anti-frictional performance.

Another example of conventional tester for roller bearings is disclosed in Published Unexamined Patent Application in Japan No. 2005-91 212, in which the lifetime test of durability of the cylindrical roller bearing is carried out by application of an edge load on a rolling contact area. With the prior roller bearing tester constructed as stated earlier, a rotating shaft is born rotationally at opposite ends thereof respectively by means of support bearings which are made of a pair of automatic aligning roller bearings. A specimen of cylindrical roller bearing is prepared between an inside circular surface of the movable housing lying around an intermediate area of the rotating shaft and an outside circular surface of the intermediate area of the rotating shaft. With the rolling bearing tester constructed as stated earlier, the center axis of the movable housing and the center axis of the rotating shaft are brought into in alignment with each other by means of the first adjusting screws and second adjusting screws each of which is prepared in pairs. With the construction as stated earlier, the radial load applied on the cylindrical roller bearing by means of the pressure device is determined with accuracy so as to prevent occurrence of the edge load to carry out the lifetime test of duration of the cylindrical roller bearing.

A further another example of prior lifetime tester for the radial roller bearing is disclosed in Published Unexamined Patent Application in Japan No. 2014-202 639, in which the stationary housing is made sufficiently higher in rigidity to carry out the reliable lifetime test for the bearing. The radial rolling bearing tester constructed as stated earlier is intended to carry out the lifetime test of the bearing. The tester for the radial roller bearing is made of the stationary housing which is made of carbon steel blank which has been subjected to forging and cutting processes.

The stationary housing as a whole is made in an integral construction inside which there is provided a lubricant sump having a cylindrical concaved bottom which is made to have an axis concentric with the central axis of the rotating shaft.

Another example of prior lifetime evaluation device for radial roller bearing is disclosed in Published Unexamined Patent Application in Japan No. H11-64 167. The lifetime evaluation device for radial roller bearing is preferred to carry out the lifetime evaluation with accuracy under the situations closer to conditions of regular usage. With the prior lifetime evaluation device for radial roller bearing constructed as stated earlier, a specimen of the test bearing interposed between rotating members of the bearing tester is stored in a casing which is raised upward by means of a compression coiled spring.

The casing having stored the test bearing therein is connected at the lower end thereof to a linkage member having a load cell. A load cylinder at the tip end thereof is pivoted to the lower end of the linkage member. Thus, variation in radial load is exerted on the test bearing by means of the load cylinder and the variable load is generated by selection in number of the rotating eccentric weight screws. With the lifetime evaluation device constructed as stated earlier, the radial load may be applied arbitrary to vary the load. Moreover, zero adjustment of the load cell may be performed the life evaluation with high precision at the condition closer to the practical use.

With the wear-proof test for the retainer in radial load tester, generally, the retainer is fastened to the rotating shaft of the radial load tester to make one revolution together with the rotating shaft to be subjected to the test load. When the retainer experiences no flex as incorporated in the engine, the retainer will be urged across a very small area against an outside ring and therefore the outside circumference of the retainer is subject to a higher contact pressure than in the engine. As a result, the surface treatment skin has torn off and thereafter the wear-proof test couldn't be executed according to the required engine conditions. With the testing device disclosed in the earlier recited Published Unexamined senior Patent Application in Japan No. H04-24 531, it is adversely required to make the testing device large scaled to resist large centrifugal load. To this end, it is needed to increase the revolution per second and the revolutionary velocity of the arms of supporting bracket to bear the specimen bearing. With the tester constructed as stated earlier, moreover, as a result of wear-proof test to make sliding contact with the outside circular surface of the retainer of the needle cage, it was shown that the sliding velocity of the retainer becomes higher compared with the actual engine because each ring for test bearings rolls through along the inside circular surface of the sun wheel to rotate on its own axis while revolving around sun wheel. In order to bear the large centrifugal load while reducing the sliding velocity down to the substantially same level with the actual engine, it is desired to increase the number of revolution of the main shaft while making the arm of the supporting bracket shorter in length. With tester constructed as stated earlier, application of the centrifugal load to the load bearing specimen is carried out to chiefly make durability test under the lubrication conditions of the two-cycle engines. Though large composite centrifugal force of revolution and rotation was applied to the needle cage, the retainer was free of urgency against a track surface or the inside circular surface of the sun wheel in the tester, so that the wear-proof test of the surface-treatment skin wasn't done under the conditions near the actual engine.

Large-scale alternation of the tester was very tough because requiring large-scale design alternation and risking high cost. With the conventional wear-proof test done in the radial load tester, the retainer is fastened to the rotating shaft of the tester as stated earlier and subjected to the test load while rotated integrally to make the sliding contact between the outside circular surface of the retainer and the inside circular surface of the outside test wheel. When the retainer has no flex as assembled in the engine, the retainer becomes urged at a very small area against the outside test wheel. Thus, as the result higher contact surface-pressure than in the actual engine affected against the outside surface of the retainer, the surface-treatment skin was torn off from the outside circular surface of the retainer and therefore the wear-proof test could not be made on the assumption of actual conditions of the engine.

SUMMARY OF THE INVENTION

The present invention has for its primary object to resolve the major problem as stated earlier, and to provide a wear-proof tester of rotary sliding system. More particularly, the present invention provides a wear-proof tester of retainer in engine needle cage, in which a retainer with no roller incorporated therein and a rotary shaft are fastened to leave a clearance between them. A radial load is applied to the retainer through the outside wheel lying outside the retainer to get the retainer flexing to thereby get the retainer coming into contact the inside circular surface of the outside wheel across the predetermined wide area. The retainer in the needle cage is subject to the composite centrifugal force of revolution and rotation on its axis, thereby getting flexed to near the retainer to contacting phase with the big end of the connecting rod to make the wear-proof test of the retainer possible. Thus, the wear-proof tester of retainer in needle cage of the present invention makes it possible to realize the wear-proof test of the retainer made of various kinds of material, besides wear-proof tests of the surface-treatment skin of the retainer.

The present invention is concerned with a wear-proof tester of retainer in needle cage, comprising a test retainer in the needle cage subjected to surface treatment, a rotating shaft around which the test retainers are mounted with more than one key to provide predetermined intervals, a casing for supporting the rotating shaft for rotation through support bearings which are arranged on a rotating shaft at locations spaced away equally from opposite ends of the retainer, a housing having a first outside wheel which is fit over around the retainer against rotation, loading means to apply a radial load through the housing and the first outside wheel at a preselected position of an outside circular surface of the retainer, driving means to rotate the rotary shaft, and lubricant supplying means to get the lubricant circulating to keep a predetermined lubrication inside the casing, and wherein the driving means is actuated to energize the loading means, the retainer is subject to a test radial load through the first outside wheel, and the retainer is warped towards the rotary shaft thanks to existence of the intervals, thereby to get the outside circular surface of the retainer making sliding contact with the inside circular surface of the outside wheel to carry out the wear-proof test of the surface treatment of the retainer.

The support bearings respectively mounted to the casing through a second outside wheel which fits in a bearing holder. Moreover, the housing is installed between the bearing holders so as to move in a direction perpendicular to an axial direction of the rotary shaft. The loading means has a loading rod to exert the radial load to the housing through a ball. Moreover, the keys fit across first key grooves on the retainer and second key grooves on the rotary shaft to fasten the retainer and the rotary shaft against rotation, the key grooves are three spaced at 120 degrees away from each other, and the loading rod applies the radial load to the retainer through the ball at a location midway between the adjacent keys.

The retainer is fit over the rotary shaft and kept axially with first side plates fastened to the housing, and the support bearings respectively fit over the rotary shaft against escape from the second outside wheel. Moreover, the casing has caps at opposite ends thereof, the caps lying at opposite ends of the rotary shaft support for rotation the rotary shaft through ball bearings, and the cap nearby the driving means supports for rotation the rotary shaft through a sealing member.

With the wear-proof tester of the retainer of the present invention, moreover, one of the caps lying nearby the casing has a lubricating port to supply the lubricant into the casing through the lubricant supplying means and another cap has a discharge port to expel the lubricant in the casing.

The needle cage is composed of the retainer and rollers retained in more than one pocket arranged circularly of the retainer, the needle cage is composed of the retainer and the rollers held more than one pocket spaced circumferentially spaced on the retainer, and incorporated in a big end of a connecting rod in a four-cycle engine. Moreover, the outside wheel is equivalent to the big end of the connecting rod. The test load set and loaded to the retainer by the load applicator is a radial load which is calculated back with the second contact area between the first outside wheel and the retainer based on the previously prepared approximate curve between the radial load and the second contact area between the outside circular surface of the retainer and the inside circular surface of the first outside wheel, after a contact surface pressure has been obtained by analyzing with the finite element method using a centrifugal force exerted to the retainer incorporated in the big end of the connecting rod and the first contact area of the retainer making contact by centrifugal force with the big end of the connecting rod.

EFFECT OF THE INVENTION

The wear-proof tester of the present invention is a wear-proof tester in which the retainer is subjected to flex in the needle cage. With the wear-proof tester, the condition the retainer gets flexed under the centrifugal force in the actual engine may be reproduced after the retainer has been flexed under the radial load to make contact with the test outside wheel. The wear-proof tester constructed as stated earlier, moreover, is compact and simple in construction. The retainer in the actual engine, when subjected to the load through the outside wheel, gets flexed to reproduce the condition in which the retainer gets flexed under the centrifugal force At this time, various tests of the PV value conditions may be carrier out under the control of the test load and rpm of the rotary shaft. The wear-proof tests of the retainer under various PV value conditions may be carried out by analysis of the relation between the radial load applied to the retainer and the contact area due to the flex of the retainer. The wear-proof tester is compact in construction, easy to make hermetical seal in the casing, easy to control the amount and the temperature of lubricant, easy to control the conditions of lubricant, and further easy to reproduce the conditions of the big end of connecting rod in four-cycle engine. With the wear-proof tester, the flexing conditions of the retainer in the actual engine may be embodied. Namely, the wear-proof test is carried out by replacement of the centrifugal force acting in a direction urging the retainer against the inside circular surface of the big end of the connecting rod with the radial load facing the center from outside of the retainer. With the wear-proof tester, moreover, as the loaded radial load and rpm may be controlled, for example, even though the load is made less to get the contact surface pressure to increase the sliding velocity, the test may be carried out under operating conditions near the actual engine, and the contact surface pressure and the sliding velocity may be freely controlled independently each other.

DETAILED DESCRIPTION OF THE INVENTION

The wear-proof tester of the present invention is preferably used for evaluation of wear-proof performance of surface treatment done on a retainer in the needle cage which is incorporated in, for example, a big end of the connecting rod used in the four-cycle engine.

Figure 7:
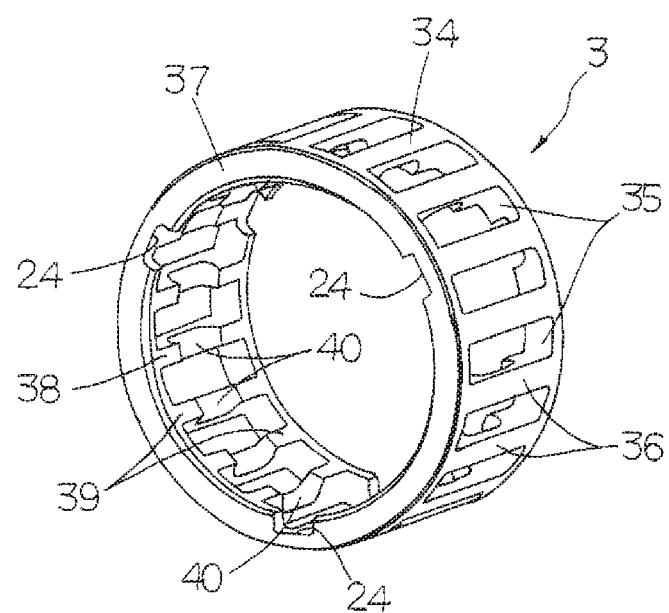
FIG. 7 is a perspective view showing a key slotted retainer.
Figure 8:
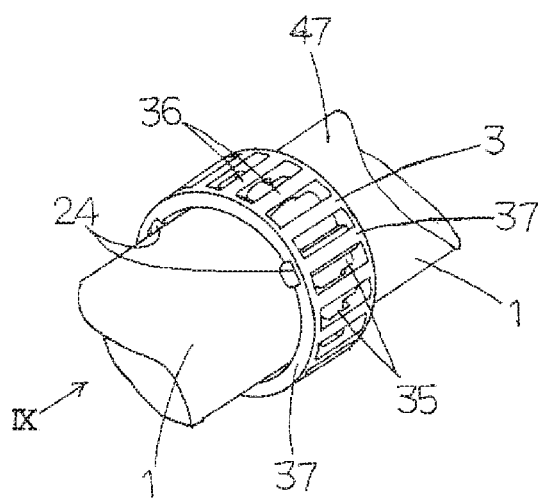
FIG. 8 is a perspective view showing the retainer fit over the rotary shaft, which are viewed after the housing case has been demounted from the assembly of FIG. 6.

A wear-proof tester in a needle cage of the present invention will be explained in detail with reference to the accompanying drawings. The wear-proof tester in a needle cage is suited, for example, to the wear-proof tester for needle cage for the surface-treated retainer for the four-cycle engines. A motor, not shown, serving as an energizing means is underneath a basement 41 on which is installed a casing 6 of the wear-proof tester. The wear-proof tester in a needle cage is constituted to bear a radial load F2 (refer to FIG. 11). The needle cage is constituted with a retainer 3 having an outside circular surface 34 subjected to surface treatment and made with more than one windows or pockets spaced circularly from each other in which rollers (not shown) fit, one to each window. With the wear-proof tester in the needle cage constructed as stated earlier, upon energizing the motor, the radial load F2 is applied to the test retainer 3 by means of a loading rod 9 and an outside wheel 2 (first wheel) serving as spring-energized loading means. The retainer 3 is loaded with a radial load which may get the contact-surface pressure similar with the actual engine acting to the retainer 3 through the loading rod 9 lying in the casing 6 which constitutes the loading means. The needle cage constituted as stated earlier is suited for assembled in the big end 2C (refer to FIG. 13) of the connecting rod in 4-cycle engine. With the wear-proof tester in the needle cage constructed as stated earlier, the outside wheel 2 is the equivalent of the big end 2C of the connecting rod in 4-cycle engine. The retainer 3 as shown in FIG. 7 is designed in a cylindrical contour adapted to fit over the rotary shaft 1 and constituted with more than one columns 36 spaced circularly to regulate the rollers from each other, more than one pockets 35 to define each roller between the adjacent columns 36, annular members 37 lying at axially opposite ends of the pockets 35. Each the column 36 is made thinner at the middle 40 thereof and thicker at opposite ends 39.

Figure 3:
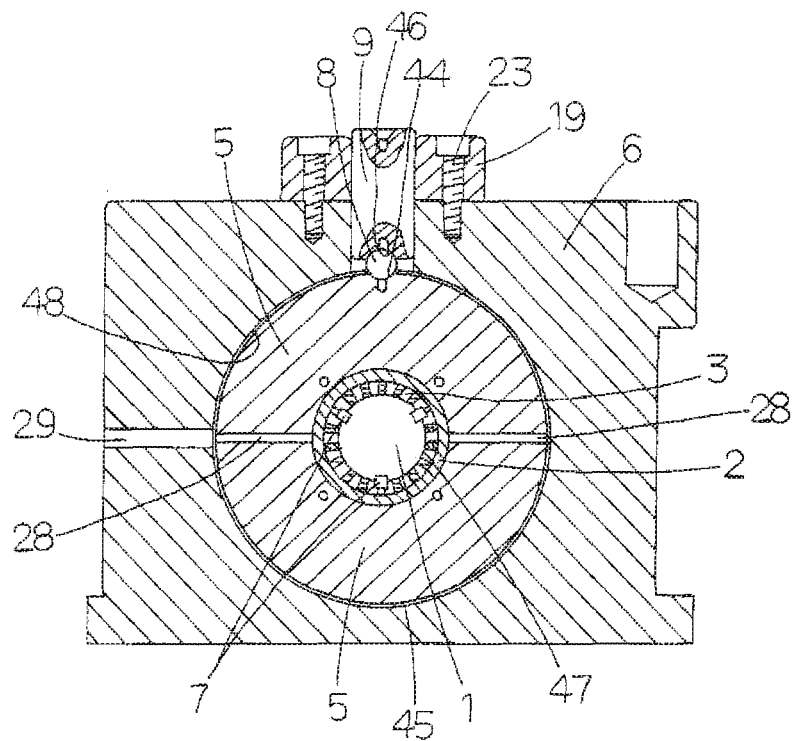
FIG. 3 is a traverse cross-section taken along the plane III-III of FIG. 2.
Figure 4:
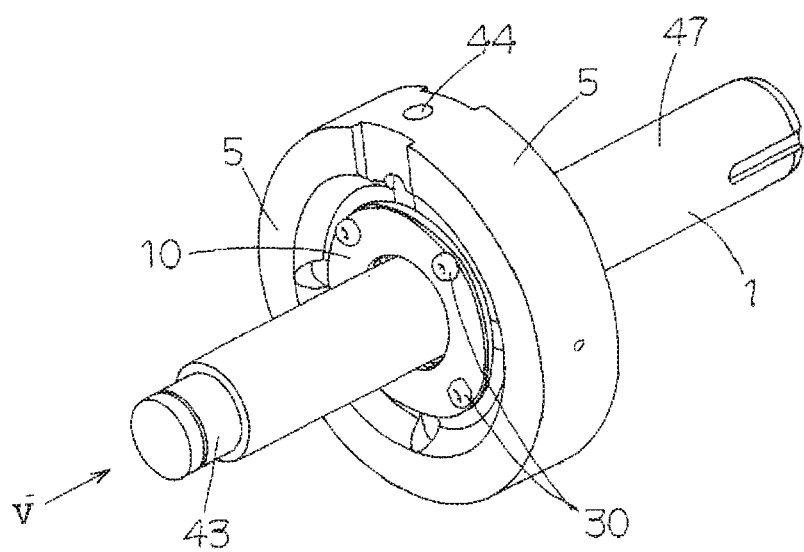
FIG. 4 is a perspective view showing an assembly in which a housing case is installed over a rotary shaft through a needle cage, the housing case being shown removed from the wear-proof tester of the retainer shown in FIG. 2.
Figure 5:
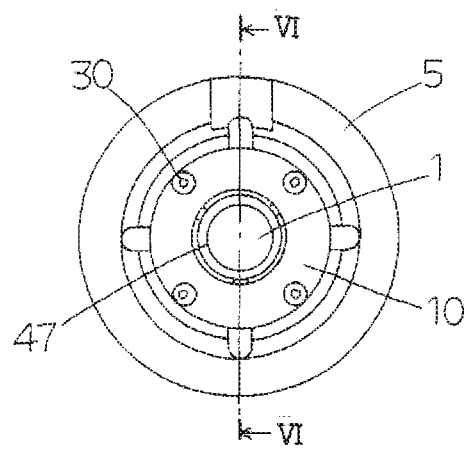
FIG. 5 is a front view showing the rotary shaft and the housing case, the view being seen in the direction V of FIG. 4.
Figure 6:
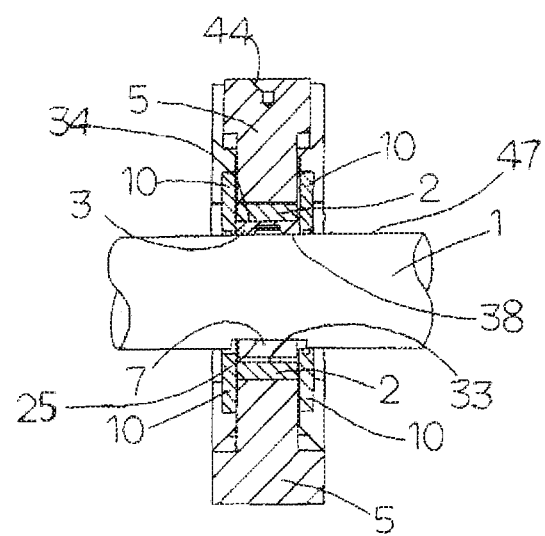
FIG. 6 is a traverse cross-section taken along the plane VI-VI of FIG. 5.
Figure 14:
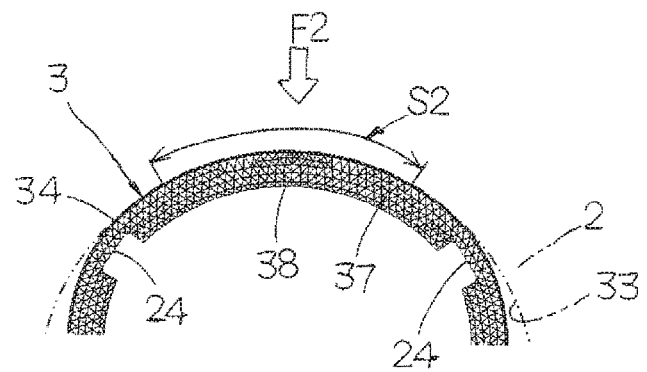
FIG. 14 is an analytic diagram showing an example of analytic models using finite element method to calculate the deformed state of the retainer using the wear-proof tester of the needle cage of the present invention.
Figure 15:
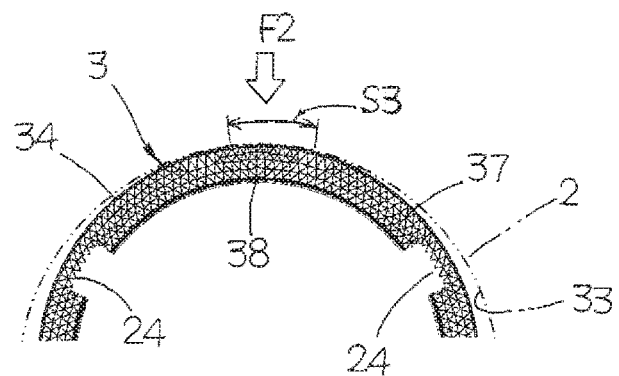
FIG. 15 is an analytic diagram showing an example of analytic models calculated using finite element method to determine the deformed state of the retainer under the radial load when the inside circular surface of the retainer makes close contact with the outside circular surface of the rotary shaft.
Figure 16:
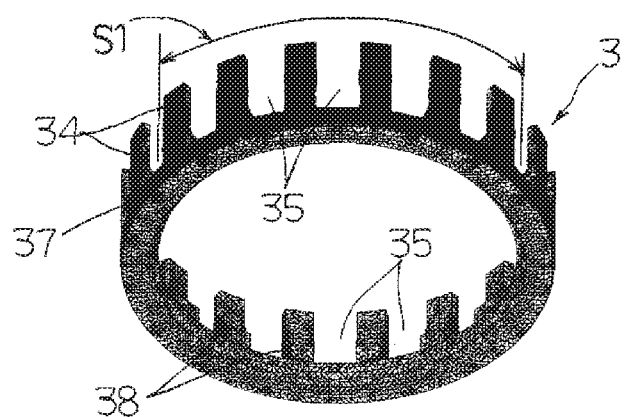
FIG. 16 is a perspective view demonstrating a contact area of the retainer flexed in the engine.

The retainer 3 has a key groove 24 (first key grooves) on an inside circular surface 38 thereof and the rotary shaft 1 has a key groove 25 (second key grooves) on an outside surface 47 thereof. Keys 7 fit into the key grooves 24 and 25 to join together the retainer 3 and the rotary shaft 1 to make rotation integrally. The key grooves 24, 25 on the retainer 3 and the rotary shaft 1 are preferably spaced at equal circular intervals, for example three grooves are spaced at 120 degrees away from each other. The retainer 3 when subjected to the radial load F2 through the test outside wheel 2 is loaded to get flexed towards the rotary shaft 1. For instance, the retainer 3 when subjected to the radial load F2 through the test outside wheel 2 is stressed to get flexed or warped towards the rotary shaft 1. The retainer 3 when subjected to the radial load F2 at the middle thereof is flexed towards the rotary shaft 1. Thus, the outside circular surface 34 of the retainer 3 in part comes into close contact with the inside circular surface 33 of the outside wheel 2. In the 4-cycle engines, for example, the retainer 3 of the needle cage incorporated in the big end 2C of the connecting rod is subjected to the centrifugal force caused by revolution while rotating on its own axis, which are caused by reciprocating movement of the connecting rod in the engine and rotating movement of the crank shaft. As a result, the retainer 3 as shown in FIG. 3 is urged by the inside circular surface 32 of big end 2C of the connecting rod to bend or warp to make sliding contact or engagement with the inside circular surface 32 over a contact area S1. With the wear-proof tester in the needle cage constructed as stated earlier, as shown in FIG. 14, the retainer 3 when subjected to the radial load F2 is compressed radially inwardly to flex to make close contact with the inside circular surface 33 of the outside test wheel 2 over the predetermined contact area S2.

Figure 1:
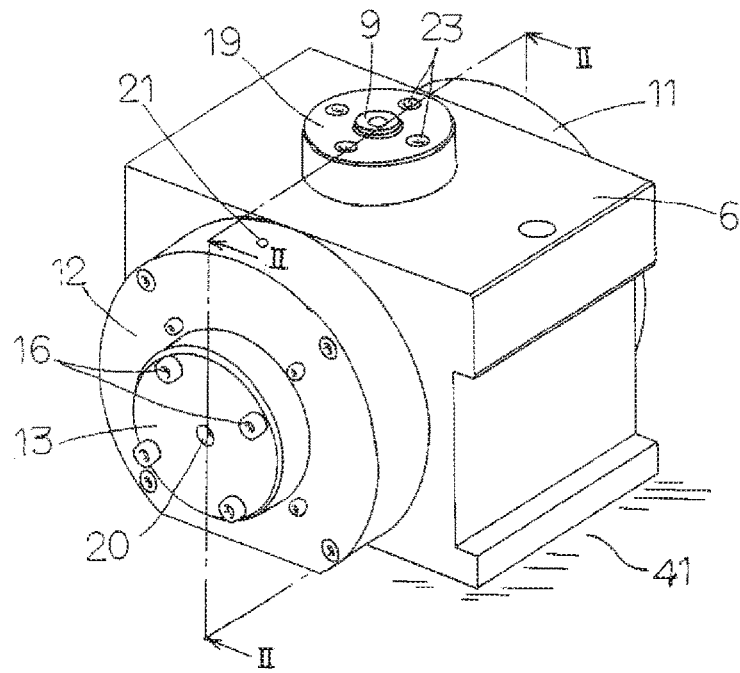
FIG. 1 is a perspective view showing an outside appearance of a wear-proof tester equipped on an outside periphery of a retainer of an engine needle cage according to the present invention.
Figure 2:
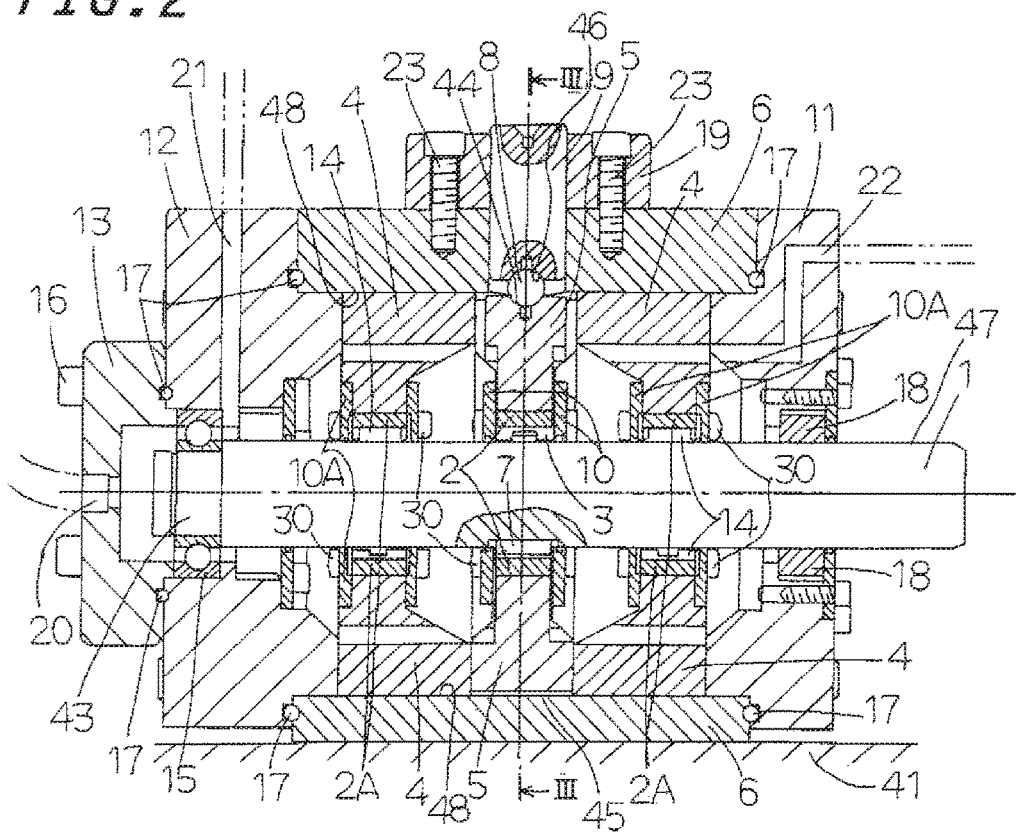
FIG. 2 is a traverse cross-section taken along the plane II-II of FIG. 1.

With the wear-proof tester constructed as stated earlier, as shown in FIGS. 1 to 3, the casing 6 has a hollow cavity 48 containing therein a housing 5 flanked by bearing holders 4 which have a through hole in which the rotary shaft 1 extends through there. The casing 6 has a sensor hole 29 to guide a sensor to monitor temperature inside the casing 6. The housing 5 has a through-hole 28 connected to the sensor hole 29 to circulate lubricant which will be described later. Moreover, the housing 5 is installed inside the casing 6 to form a clearance 45 between the bearing holders 4 described in detail later and the lower side of the hollow cavity 48 and the bearing holders 4. The housing 5 is allowed to move up and down between the bearing holders 4. The outside wheels 2A (the second outside wheels) fit into the hollow cavities in the housing 5 and paired bearing holders 4. The rotary shaft 1 extends across the outside wheel 2, which fits over the housing 5, through the test retainer 3. The housing 5 has therein the outside wheel 2 which fits in such a manner restricted against rotation with respect to the outside circumference of the retainer 3. Outside wheels 2A born for rotation with support bearings 14 on the rotary shaft 1 fit in a bearing holder 4. The support bearings 14 are arranged isolated equally away from the opposite ends of the retainer 3. It will be thus understood that the support bearings 4 are respectively mounted to the casing 6 through the outside wheels 2A which fits over the bearing holders 4. The housing 5 is arranged movably in radial direction with respect to the bearing holders 4. The outside wheels 2, 2A at opposite sides thereof are secured with side plates 10 and fastening bolts 30 so as not to escape off from the cavities in the housing 5 and bearing holders 4. The retainer 3, moreover, fits over the rotary shaft 1 and kept axially with side plates 10 (first side plate) against coming off from the outside wheel 2. Moreover, the support bearings 14 are fit over the rotary shaft 1 so as not to escape off from the outside wheel 2A and further held in axial direction with a side plate 10A (second side plate) secured to the bearing holder 4. The casing 6 at one end thereof has a first cap 11 which is bolted at 31 with a sealing member 18 to seal up around the rotary shaft 1, and at the other end thereof a second cap 12 supported with a ball bearing 15. On the end surface of the second cap 12, there is fastened with fastening bolts 16 a third cap 13 which has a lubricating port 20 to feed lubricant into the wear-proof tester. Moreover, an O-ring 17 is installed between abutment surfaces of the second cap 12 and the third cap 13 and another O-ring 17 is installed between abutment surfaces of the first cap 11 and the second cap 12, so that the casing 6 is sealed hermetically to protect the lubricant against leakage out of the casing 6. The paired support bearings 14 serves for bearing the rotary shaft 1 against the radial load F2. With the embodiment disclosed herein, the third cap 13 has the lubricating port 20, and the first cap 11 and the second cap 12 respectively have outlet ports 22 for circulation of lubricant. Thus, lubricant is allowed to circulating in the casing 6.

With the wear-proof tester constructed as stated, the loading rod 9 to apply the radial load F2 using a spring (not shown) is inserted movably into a through-hole 42 made in the upper portion of the casing 6 to apply the radial load F2 to the outside wheel 2 through the housing 5. With the loading means constructed as stated earlier, the radial load F2 is applied to the circumference or circular surface 34 of the retainer 3 through the housing 5 and the outside wheel 2. The loading rod 9 serving as loading means is so supported with the support member 19 as to move through-hole 42 in the casing 6. The support member 19 is secured to the casing 6 by means of fastening bolts 23. With the wear-proof tester constructed as stated, the loading point is provided to apply the load to the housing 5 through a ball 8 which fits between recesses 44 and 46 one of which is made in an upper surface of the housing 5 and the other is made in a lower surface of the loading rod 9. Thus, the loading rod 9 is constituted to apply the load to the housing 5 through the ball 8. The loading rod 9 is subjected to the test load through, for example, a spring (not shown). The test load is detected with a load cell attached to loading rod 9. The ball 8 lying between the loading rod 9 and the housing 5 is to make sure of the load uniform across the outside circular surface 34 of the retainer 3. The outside circular surface 34 of the retainer 3 is regulated to make contact across a predetermined area with the inside circular surface 33 of the test outside wheel 2. An amount of flex is calculated previously when the radial load F2 is applied to the retainer 3 to determined the contact surface with the outside wheel 2. An amount of the radial load F2 loaded on the retainer 3 is regulated to adjust the contact area of outside wheel 2 with the flexed retainer 3.

Figure 9:
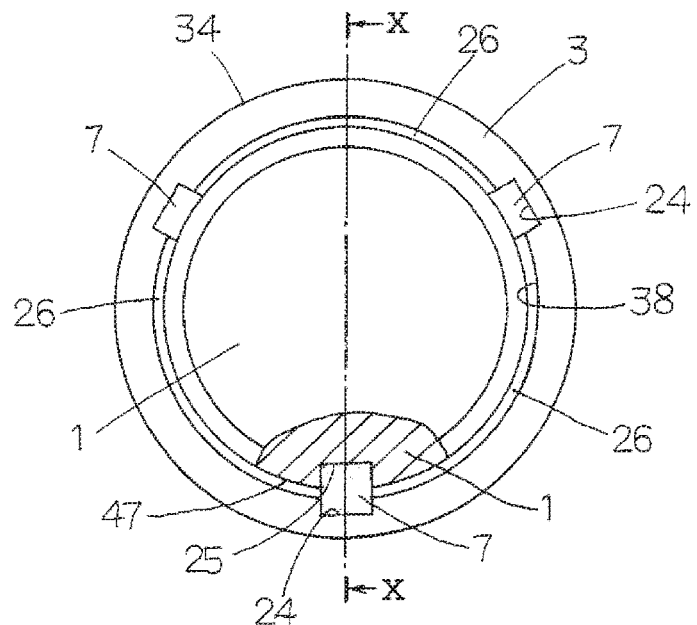
FIG. 9 is a front elevation of the rotary shaft of FIG. 8 viewed in the direction IX of FIG. 8, the view being broken away in part and enlarged exaggeratingly to show a clearance made between the retainer and the rotary shaft.
Figure 10:
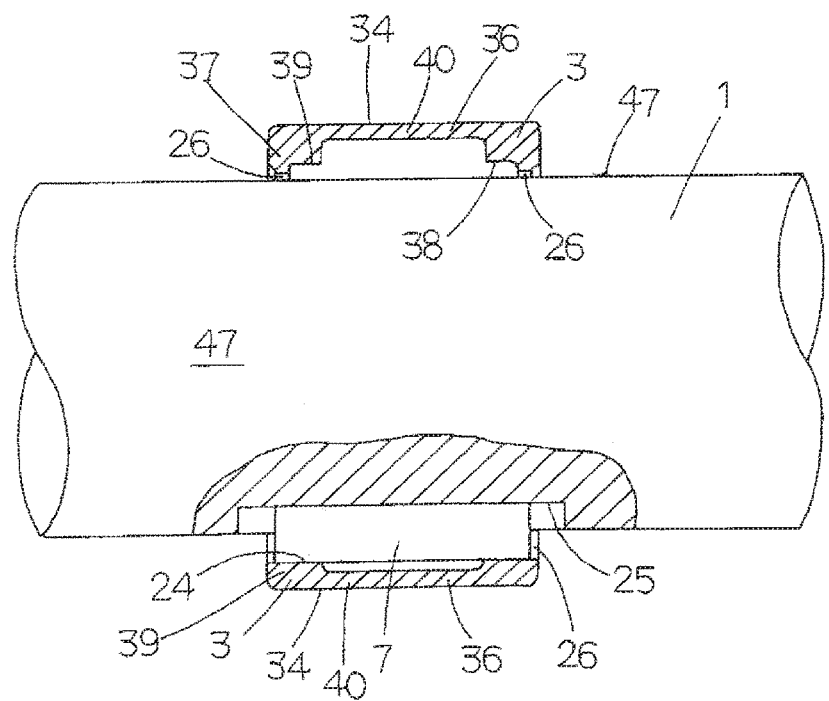
FIG. 10 is a side elevation, partially broken away, of the rotary shaft, the view being taken along the plane X-X of FIG. 9.
Figure 11:
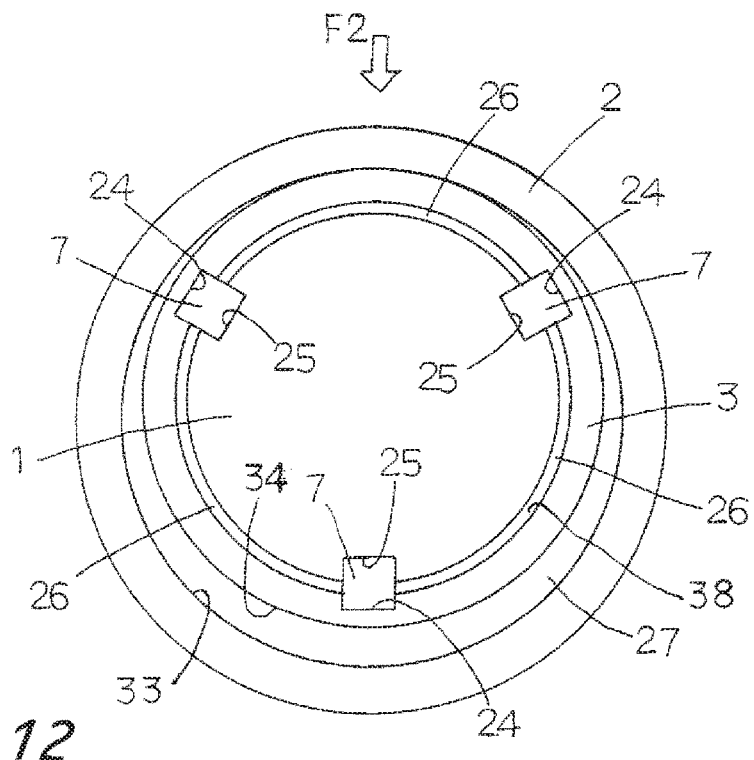
FIG. 11 is an explanatory view showing a wear-proof tester in which the retainer is supported on the rotary shaft with two keys to keep clearances and the retainer is arranged inside the test outside wheels, more especially showing exaggeratingly the clearance between the rotary shaft and the retainer and showing the eccentric relation between the outside wheel and the rotary shaft and further showing the phase where the retainer is subject to the outside test load at the intermediate of a zone supported with two keys to make flex to come into contact with the inside circular surface of the outside wheel.
Figure 12:
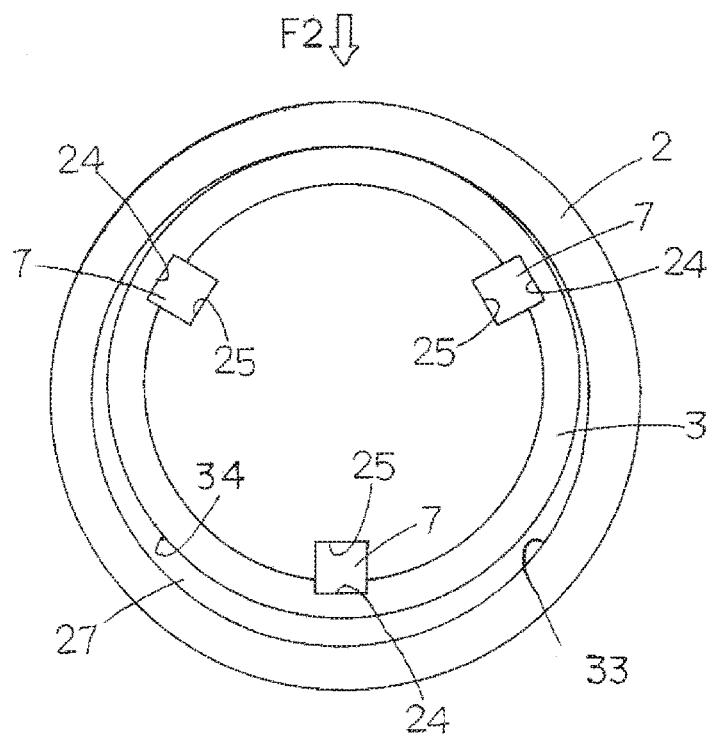
FIG. 12 is an explanatory view showing exaggeratingly an eccentric phase between the outside wheel and the rotary shaft to illustrate the state where the test load is applied to the retainer which is kept in such a situation that the inside circular surface of the retainer is made close engagement with the outside circular surface of the rotary shaft to keep the retainer against flex.

The wear-proof tester of the present invention, especially as shown in FIGS. 9 and 11, has the feature that the rotary shaft 1 is surrounded with the retainer 3 and connected to the retainer 3 surrounded with more than one key 7 (three in FIGS. 9 and 11) to keep a preselected clearance 26 between them and the radial load F2 is applied to the retainer 3 at a location midway between the adjacent keys 7. Moreover, the retainer 3 is installed to provide an annular clearance 27 between the inside circular 33 of the outside wheel 2 and the outside circular surface 34 of the retainer 3. The wear-proof tester of the retainer 3 constructed as stated just above is a wear-proof tester of rotary sliding system in which the radial load F2 is applied to the retainer 3 while the outside circular surface 34 of the retainer 3 is urged to the inside circular surface 33 of the test outside wheel 2. Moreover, the inside circular surface 38 of the retainer 3 is fastened and supported in the rotating direction to the rotary shaft 1 by means of three pieces of the fastening keys 7 which are circumferentially spaced at equal intervals at 120 degrees away from each other. There is provided the clearances 26 between the inside circular surface 38 of the retainer 3 and the outside circular surface 47 of the rotary shaft 1, other than the locations supported directly with the keys 7. The keys 7 arranged to straddle over the retainer 3 and the rotary shaft 1 and fit into key grooves 24 in the retainer 3 and in key grooves 25 in the rotary shaft 1 to fasten the retainer 3 and the rotary shaft 1 in the rotating direction. Thus, three keys 7 are arranged spaced at 120 degrees away from each other around the rotary shaft 1. The loading rod 9 is located midway between paired adjacent keys 7 to apply with good balance the radial load F2 to the retainer 3. Even if the inside circular surface 38 of the retainer 3 as shown in FIG. 12 is kept in close contact to the outside circular surface 47 of the rotary shaft 1 with no clearance between them, the retainer 3 is kept against warp or bending towards the rotary shaft 1 and therefore the outside circular surface 34 of the retainer 3 comes into contact across a narrow contact area S3 thereof with the inside circular surface 33 of the test outside wheel 2. Thus, it will be fear that the contact surface pressure becomes too high and the retainer 3 becomes far apart from the condition of the retainer 3 in the actual engine. With the wear-proof tester in the needle cage, it is very critical to provide the predetermined clearance 26 between the inside circular surface 38 of the retainer 3 and the outside circular surface 47 of the rotary shaft 1 to get the retainer 3 approaching the contact condition with the big end 2C of the connecting rod.

With the wear-proof tester of the retainer 3, moreover, the lubricant gets circulated in the casing 6 to keep the environment equivalent to the four-cycle engine. In order to get lubricant circulating in the casing 6, moreover, there is provided lubricant supplier to get lubricant circulating. With the wear-proof tester of the retainer 3, the first cap 11, second cap 12 and the third cap 13 are installed on the opposite ends of the casing 6 through O-rings 17. The second cap 12 fit over one end 43 of the rotary shaft 1 supports for rotation the rotary shaft 1 through a ball bearing 15. The first cap 11 fit on the other end nearby the driving means of the rotary shaft 1 supports for rotation the rotary shaft 1 through a sealing member 18. Thus, the casing 6 is made in a hermetically closed construction having spaces including the clearances 26, 27 to reserve therein oil to lubricate the specimen retainer 3. The key grooves 24, 25 are cut on the inside circular surface 38 of the retainer 3 and the outside circular surface 47 of the rotary shaft 1, respectively. Moreover, the third cap 13 fastened to the second cap 12 has the lubricating port 20 to feed lubricant from the lubricant supplying means (not shown) into the casing 6. The first cap 11 opposite to the second cap 12 has the outlet port 22 to expel the lubricant in the casing 6. The second cap 12 also has a discharge port 21 to expel the lubricant in the casing 6.

(1) Regarding centrifugal force exerted on the retainer 3 in the actual engine: The retainer 3 of the needle cage assembled in the big end 2C of the connecting rod in the actual engine is subjected to the centrifugal force caused by revolution while rotating on its own axis, which are caused by reciprocating movement of the connecting rod in the engine and rotating movement of the crank shaft. The centrifugal force F1 is exerted on the retainer 3 due to the revolution recited earlier. The centrifugal force F1 works in the direction to urge the outside circular surface 34 of the retainer 3 against the inside circular surface 32 of the connecting rod big end 2C. The centrifugal force F1 may be obtained with reference to a mass m1 of the retainer 3, a mass m2 of needle rollers in part assembled in the retainer 3, a radius r of rotating crank shaft of the retainer 3, and the number n of rotation. Accordingly, assuming the angular velocity of the number n of rpm is $\omega$ (rad/s), the radial load F2 will be obtained by $F2 = (m1+m2) \times r \times \omega^2$.

(2) Regarding PV value: The sliding contact location is usually determined after investigation of PV value. The PV value is represented by the product of a load per unit area or contact surface pressure P and a sliding velocity V. The PV value is commonly employed to determine an operable range of the sliding bearings. The wear-proof test is carried out after the contact pressure surface P2 and sliding velocity V2 are determined respectively in compliance with the sliding contact conditions of the retainer 3 used in the actual engine.

(3) Regarding surface treatment of the retainer 3: The retainer 3 is made of steal and guided on the outside surface thereof. The retainer 3 comes in sliding contact with the inside circular surface 32 of the big end 2C of the connecting rod. The retainer 3 is subjected to surface treatment of non-ferrous metals such as cupper, silver and so on to prevent any wear and heating caused by metal-to-metal engagement of the parts or components.

Next, the procedures to set the radial load applied to the test retainer 3 using the wear-proof tester of the present invention will be explained with reference to FIG. 19. Now assuming the commonly-used 4-cycle engine, example of procedure to calculate the radial load F2 applied to the retainer 3 in the wear-proof tester will be explained hereinafter with reference to FIG. 19. The test retainer 3 is incorporated in the needle cage in the big end of the connecting rod. The needle cage for the connecting rod big end has the high rigidity able to resist against high load. Moreover, the test retainer 3 has roller pockets to hold the rollers therein on both the outside circular surface and the inside circular surface. The set test load F2 will be loaded by a load applicator according to the following procedure. First, the contact surface pressure P1 is obtained by the analysis of finite element method using the centrifugal force F1 acting on the retainer 3 incorporated in the big end 2C of the connecting rod and the first contact area S1 of the retainer 3 urged by the centrifugal force F1 to come into contact with the big end 2C of the connecting rod. Then, the radial load F2 is obtained by counting backward which is carried out in response to the contact surface S between the outside wheel 2 and the retainer 3 on the basis of the approximate curve of the radial load F and the contact area S between the outside circular surface 34 of the preliminarily made retainer 3 and the inside circular surface 33.

Figure 13:
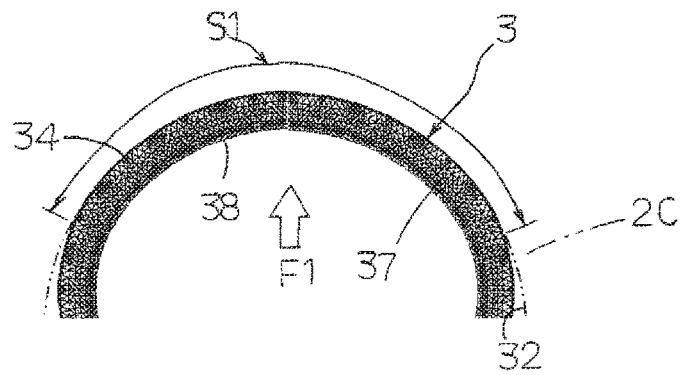
FIG. 13 is an analytic diagram showing an example of analytic models using finite element method to calculate the deformed state using finite element method at the time when the retainer has come into contact with the inside circular surface of the big end of the connecting rod.
Figure 19:
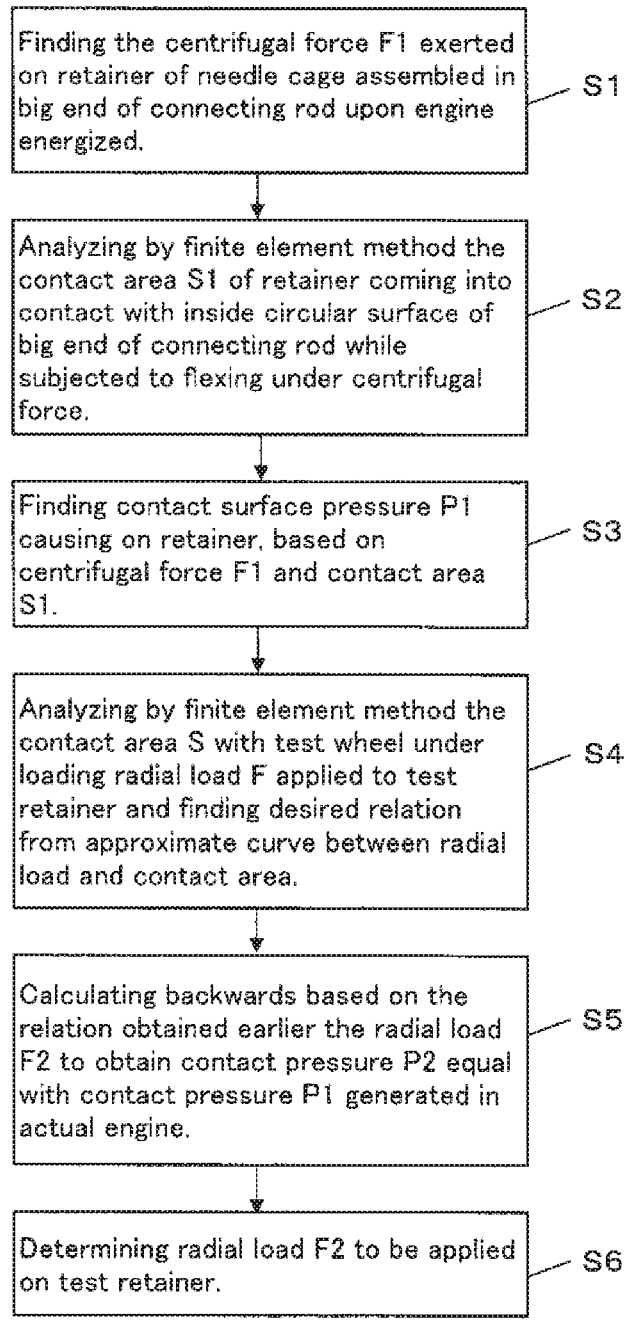
FIG. 19 is a flow chart explaining a method of setting test load using wear-proof tester for the retainer in the needle cage of the present invention.

More definitely, the centrifugal force F1 is obtained as shown in FIGS. 13 and 19. The centrifugal force F1 in the engine is referred to the value applied to the retainer 3 when the engine is driven at a predetermined rpm of engine. An amount of flexure when the obtained centrifugal force F1 is loaded to the analysis model of the retainer 3 is calculated by finite element method (Step S1). The acting direction of the loaded centrifugal force F1 is determined to a direction acting outwardly from the inside of the analytic model of the retainer 3 so as to make sure of the same condition as the retainer 3 is subjected to the centrifugal force F1 in the actual engine. There is provided a condition in which the outside circular surface 34 of the retainer 3 in analytic model makes close contact with the counterpart or the inside circular surface 32 of the big end 2C of the connecting rod to reproduce a situation in which the outside circular surface 34 of the retainer 3 is urged to the counterpart or the inside circular surface 32 of the big end 2C of the connecting rod. A contact area S1 is obtained in which a flexed area of the outside circular surface 34 of analytic model of the retainer 3 makes close contact with the inside circular surface 32 of the big end 2C of the connecting rod (Step S2). The contact pressure P1 (P1=F1/S1) is derived based on the centrifugal force F1 obtained from the conditions of actual engines and contact area S1 tentatively calculated with finite element method (Step S3). The sliding velocity V1 of the outside circular surface 34 of the retainer 3 relatively to the inside circular surface 32 of the big end 2C of the connecting rod is obtained based on the crank radius and the rpm of the engine or the number of revolution of the output shaft. Then, the PV value (PV=P1/V1) is given from the obtained contact surface pressure P1 and the sliding velocity V1.

Figure 17:
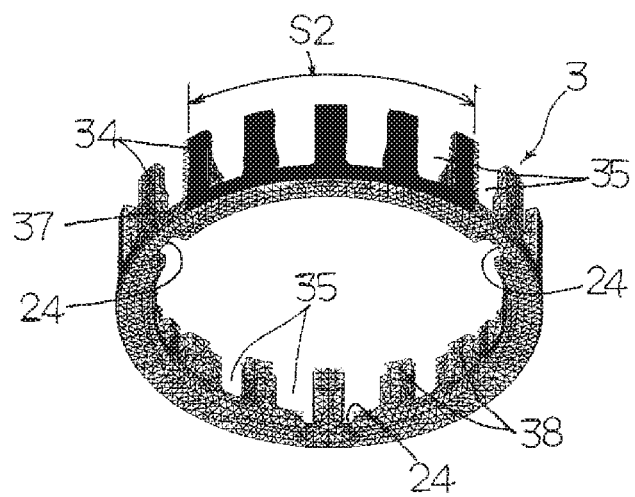
FIG. 17 is a perspective view of the retainer to demonstrate one example of analysis models of the retainer when a clearance is provided between the retainer and the rotary shaft in a test method using wear-proof tester for the retainer in the needle cage of the present invention.
Figure 18:
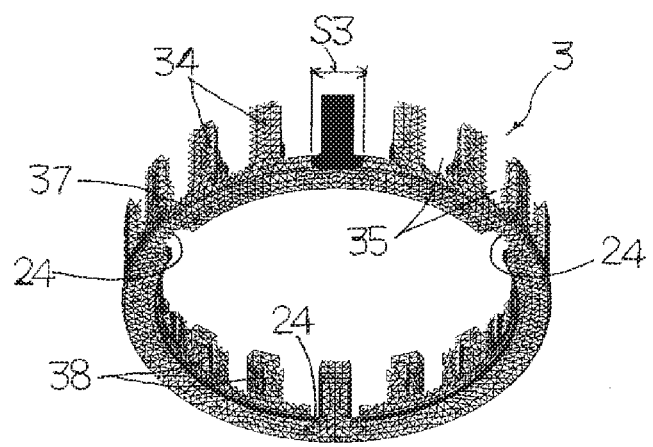
FIG. 18 is a perspective view of the retainer to demonstrate one example of analysis models of the retainer when no clearance is provided between the retainer and the rotary shaft in a test method using wear-proof tester for the retainer in the needle cage of the present invention.

Next, the condition will be determined that brings the test PV value of the wear-proof tester of the retainer 3 of the present invention into matching with the PV value of the wear-proof tester of the retainer 3 in the present invention. The contact area S2 when the retainer 3 is subjected to the radial load F2 is determined using the finite element method (Step S4). The analytic model configuration of the retainer 3, as shown in FIGS. 14 and 17, is the inside circular surface 38 of the retainer 3 having key grooves 24 thereon. The radial load F2 to obtain the contact surface pressure P2 necessary for the test retainer 3 is derived back based on the relational expression given from approximate curves of the radial load F and the contact area S (Step S5). Because of keeping the contact surface pressure P2 equivalent with the contact surface pressure P1 of the actual engine, the radial load F2 loaded to the test retainer 3 is derived from the graphic chart, not shown, which has previously prepared to show the relation of radial load F and the contact area S (Step S6). Though the retainer 3 in the actual engine is made flexed entirely owing to the centrifugal force F1, the retainer 3 in the wear-proof tester of the present invention is made flexed across only the range born with the fastening keys 7 under the load to escape towards the rotary shaft 1, so that the contact area of the retainer 3 is made less compared with the actual engine. Difference of the contact area with the actual engine depends on the number of the keys 7 to bear the test retainer 3. With the wear-proof tester of the retainer constructed as stated earlier, the contact surface pressure P2 and the sliding velocity V2 are controlled independently from each other.

Next, the method to carry out the wear-proof testing of the test carrier 3 using the wear-proof tester of the present invention will be explained below. The wear-proof testing method of the retainer 3 is to test the durability of the surface-treatment on the retainer 3 using the wear-proof testing means constructed as stated earlier. To this end, based on the contact surface pressure P1 (=F1/S1) derived from the centrifugal force F1 loaded to the retainer 3 in the needle cage assembled in the connecting rod and the contact area S1 where the inside circular surface 33 of the first outside wheel 2 and the outside circular surface 34 of retainer 3 come into contact with each other and the PV value composed of the sliding velocity V1 of the outside circular surface 34 of the retainer 3 making contact with the first test outside wheel 2, the contact area S2 corresponding to the contact surface pressure P1 of the retainer 3 and the radial load F2 corresponding to the contact area S2 are derived to obtain the sliding velocity V2 equivalent to the PV value of the actual engine, calculating the number N of rotation of the rotary shaft 1 and carrying out the test with the radial load F2 and the number N of rotation. With the method to carry out the wear-proof testing as stated earlier, when the PV value of the retainer 3 obtained by the tester is within the predetermined range, the retainer 3 is evaluated that the surface treatment has no damage and keeps the wear-proof property. Moreover, after the contact area S2 is obtained between the retainer 3 and the test outside wheel 2 the contact surface pressure P1 and the sliding velocity like the actual engine are given to do sliding contact to carry out the wear-proof test of the surface treatment applied to outside circular surface 34 of the retainer 3.

What is claimed is:

1. A wear-proof tester for a retainer in needle cage, comprising: a test retainer in the needle cage subjected to surface treatment, a rotating shaft around which the test retainers are mounted with more than one key to provide predetermined intervals, a casing for supporting the rotating shaft for rotation through support bearings which are arranged on a rotating shaft at locations spaced away equally from opposite ends of the retainer, a housing having a first outside wheel which is fit over around the retainer against rotation, loading means to apply a radial load through the housing and the first outside wheel at a preselected position of an outside circular surface of the retainer, driving means to rotate the rotary shaft, and lubricant supplying means to get the lubricant circulating to keep a predetermined lubrication inside the casing;

wherein the driving means is actuated to energize the loading means, the retainer is subject to a test radial load through the first outside wheel, and the retainer is warped towards the rotary shaft thanks to existence of the intervals, thereby to get the outside circular surface of the retainer making sliding contact with the inside circular surface of the outside wheel to carry out the wear-proof test of the surface treatment of the retainer.

2. The wear-proof tester for the retainer in the needle cage described in claim 1, wherein the support bearings respectively mounted to the casing through a second outside wheel which fits in a bearing holder.

3. The wear-proof tester for the retainer in the needle cage described in claim 2, wherein the housing is installed between the bearing holders so as to move in a direction perpendicular to an axial direction of the rotary shaft.

4. The wear-proof tester for the retainer in the needle cage described in claim 1, wherein the loading means has a loading rod to exert the radial load to the housing through a ball.

5. The wear-proof tester for the retainer in the needle cage described in claim 4, wherein the keys fit across first key grooves on the retainer and second key grooves on the rotary shaft to fasten the retainer and the rotary shaft against rotation, the key grooves are three spaced at 120 degrees away from each other, and the loading rod applies the radial load to the retainer through the ball at a location midway between the adjacent keys.

6. The wear-proof tester for the retainer in the needle cage described in claim 1, wherein a roller bearing cage constructed as defined in claim 5, wherein the retainer is fit over the rotary shaft and kept axially with first side plates fastened to the housing, and the support bearings respectively fit over the rotary shaft against escape from the second outside wheel.

7. The wear-proof tester for the retainer in the needle cage described in claim 1, wherein the casing has caps at opposite ends thereof, the caps lying at opposite ends of the rotary shaft to support for rotation the rotary shaft through ball bearings, and the cap nearby the driving means supports for rotation the rotary shaft through a sealing member.

8. The wear-proof tester for the retainer in the needle cage described in claim 1, wherein one of the caps lying nearby the casing has a lubricating port to supply the lubricant into the casing through the lubricant supplying means, and another cap has a discharge port to expel the lubricant in the casing.

9. The wear-proof tester for the retainer in the needle cage described in claim 1, wherein the needle cage is composed of the retainer and rollers retained in more than one pocket arranged circularly of the retainer, the needle cage being incorporated in a big end of a connecting rod in a four-cycle engine.

10. The wear-proof tester for the retainer in the needle cage described in claim 9, wherein the outside wheel is equivalent to the big end of the connecting rod.

11. The wear-proof tester for the retainer in the needle cage described in claim 10, wherein a test load set and loaded to the retainer by the load applicator is a radial load which is calculated back with the second contact area between the first outside wheel and the retainer based on the previously prepared approximate curve between the radial load and the second contact area between the outside circular surface of the retainer and the inside circular surface of the first outside wheel, after a contact surface pressure has been obtained by analyzing with the finite element method using a centrifugal force exerted to the retainer incorporated in the big end of the connecting rod and the first contact area of the retainer making contact by centrifugal force with the big end of the connecting rod.

\* \* \* \* \*